US008591409B2

(12) United States Patent
Wenchell (10) Patent No.: US 8,591,409 B2
(45) Date of Patent: Nov. 26, 2013

(54) SURGICAL HAND ACCESS APPARATUS

(75) Inventor: Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 677 days.

(21) Appl. No.: 11/594,270

(22) Filed: Nov. 7, 2006

(65) Prior Publication Data

US 2007/0055107 A1    Mar. 8, 2007

Related U.S. Application Data

(62) Division of application No. 10/832,224, filed on Apr. 26, 2004, now Pat. No. 7,153,261.

(60) Provisional application No. 60/465,932, filed on Apr. 25, 2003.

(51) Int. Cl.
*A61B 1/32* (2006.01)

(52) U.S. Cl.
USPC .......................................... 600/208; 600/210

(58) Field of Classification Search
USPC ......... 600/174, 185, 192, 206–208, 210, 213, 600/215–216
See application file for complete search history.

(56) References Cited

U.S. PATENT DOCUMENTS

| | | | |
|---|---|---|---|
| 2,305,289 A | 12/1942 | Coburg | |
| 3,332,417 A | 7/1967 | Blanford et al. | |
| 3,341,394 A | 9/1967 | Kinney | |
| 3,427,226 A | 2/1969 | McNeely | |
| 3,427,227 A | 2/1969 | Chamberlin | |
| 4,041,203 A | 8/1977 | Brock et al. | |
| 4,069,913 A | 1/1978 | Harrigan | |
| 4,447,237 A | 5/1984 | Frisch et al. | |
| 4,984,564 A | 1/1991 | Yuen | |
| 5,159,921 A | 11/1992 | Hoover | |
| 5,213,114 A * | 5/1993 | Bailey, Jr. | 128/849 |
| 5,342,385 A | 8/1994 | Norelli et al. | |
| 5,360,417 A | 11/1994 | Gravener et al. | |
| 5,366,478 A | 11/1994 | Brinkerhoff et al. | |
| 5,368,545 A | 11/1994 | Schaller et al. | |
| 5,411,483 A | 5/1995 | Loomas et al. | |
| 5,480,410 A | 1/1996 | Cuschieri et al. | |

(Continued)

FOREIGN PATENT DOCUMENTS

DE    37 37 121    5/1989
DE    37 37 121    11/1989

(Continued)

OTHER PUBLICATIONS

US 7,282,043, 10/2007, Racenet et al. (withdrawn).

(Continued)

*Primary Examiner* — Nicholas Woodall
*Assistant Examiner* — Larry E Waggle, Jr.

(57) ABSTRACT

A hand access device includes a housing defining a longitudinal axis and having a passageway therethrough dimensioned to permit passage of a surgeon's arm and a fabric seal mounted within the opening and being dimensioned to form a substantial sealing relation with the surgeon's arm. The fabric seal is elongated extending along the longitudinal axis and may define a general hour glass configuration. A pair of flexible bands may be mounted about the fabric seal. The flexible bands are adapted to engage an outer surface of the seal to bias the fabric seal to a closed position thereof.

9 Claims, 7 Drawing Sheets

(56) References Cited

U.S. PATENT DOCUMENTS

| | | | |
|---|---|---|---|
| 5,514,133 A | 5/1996 | Golub et al. | |
| 5,520,610 A | 5/1996 | Giglio et al. | |
| 5,522,791 A | 6/1996 | Leyva | |
| 5,524,644 A | 6/1996 | Crook | |
| 5,526,536 A | 6/1996 | Cartmill | |
| 5,545,179 A * | 8/1996 | Williamson, IV | 606/213 |
| 5,572,743 A | 11/1996 | Yavitz | |
| 5,603,702 A | 2/1997 | Smith et al. | |
| 5,634,911 A | 6/1997 | Hermann et al. | |
| 5,634,931 A | 6/1997 | Kugel | |
| 5,634,937 A * | 6/1997 | Mollenauer et al. | 606/213 |
| 5,636,645 A | 6/1997 | Ou | |
| 5,637,937 A | 6/1997 | Nakajima | |
| 5,639,937 A | 6/1997 | Hover et al. | |
| 5,640,977 A | 6/1997 | Leahy et al. | |
| 5,649,550 A | 7/1997 | Crook | |
| 5,653,705 A | 8/1997 | de la Torre et al. | |
| 5,672,168 A | 9/1997 | de la Torre et al. | |
| 5,741,298 A | 4/1998 | MacLeod | |
| 5,803,921 A | 9/1998 | Bonadio | |
| 5,810,721 A | 9/1998 | Mueller et al. | |
| 5,813,409 A | 9/1998 | Leahy et al. | |
| 5,832,925 A | 11/1998 | Rothrum | |
| 5,853,395 A | 12/1998 | Crook et al. | |
| 5,899,208 A | 5/1999 | Bonadio | |
| 5,906,577 A | 5/1999 | Beane et al. | |
| 5,947,922 A | 9/1999 | MacLeod | |
| 5,957,913 A | 9/1999 | de la Torre et al. | |
| 5,964,781 A | 10/1999 | Mollenauer et al. | |
| 5,997,515 A | 12/1999 | de la Torre et al. | |
| 6,024,736 A | 2/2000 | de la Torre et al. | |
| 6,033,426 A * | 3/2000 | Kaji | 606/213 |
| 6,033,428 A | 3/2000 | Sardella | |
| 6,042,573 A | 3/2000 | Lucey | |
| 6,048,309 A | 4/2000 | Flom et al. | |
| 6,077,288 A * | 6/2000 | Shimomura et al. | 606/185 |
| 6,079,692 A | 6/2000 | Powell | |
| 6,086,570 A | 7/2000 | Aboul-hosn et al. | |
| 6,110,154 A | 8/2000 | Shimomura et al. | |
| 6,113,623 A | 9/2000 | Sgro | |
| 6,142,935 A | 11/2000 | Flom et al. | |
| 6,142,936 A | 11/2000 | Beane et al. | |
| 6,149,642 A | 11/2000 | Gerhart et al. | |
| 6,159,200 A | 12/2000 | Verdura et al. | |
| 6,162,172 A | 12/2000 | Cosgrove et al. | |
| 6,238,373 B1 | 5/2001 | de la Torre et al. | |
| 6,254,533 B1 | 7/2001 | Fadem et al. | |
| 6,254,534 B1 | 7/2001 | Butler et al. | |
| 6,276,661 B1 | 8/2001 | Laird | |
| 6,315,770 B1 | 11/2001 | de la Torre et al. | |
| 6,319,246 B1 * | 11/2001 | de la Torre et al. | 606/1 |
| 6,382,211 B1 | 5/2002 | Crook | |
| 6,440,063 B1 | 8/2002 | Beane | |
| 6,450,983 B1 | 9/2002 | Rambo | |
| 6,471,714 B1 | 10/2002 | Kim | |
| 6,482,181 B1 * | 11/2002 | Racenet et al. | 604/167.06 |
| 6,482,214 B1 | 11/2002 | Sidor et al. | |
| 6,485,467 B1 * | 11/2002 | Crook et al. | 604/174 |
| 6,578,577 B2 | 6/2003 | Bonadio et al. | |
| 6,610,031 B1 | 8/2003 | Chin | |
| 6,616,685 B2 | 9/2003 | Rousseau | |
| 6,702,787 B2 | 3/2004 | Racenet et al. | |
| 6,723,044 B2 | 4/2004 | Pulford et al. | |
| 6,964,674 B1 | 11/2005 | Matsuura et al. | |
| 7,244,244 B2 | 7/2007 | Racenet et al. | |
| 7,470,255 B2 | 12/2008 | Stearns et al. | |
| 7,736,306 B2 | 6/2010 | Brustad et al. | |
| 2002/0072762 A1 * | 6/2002 | Bonadio et al. | 606/192 |
| 2002/0183594 A1 * | 12/2002 | Beane et al. | 600/207 |
| 2003/0078478 A1 | 4/2003 | Bonadio | |
| 2004/0059297 A1 | 3/2004 | Racenet et al. | |
| 2004/0138703 A1 | 7/2004 | Alleyne | |
| 2005/0148823 A1 | 7/2005 | Vaugh et al. | |
| 2006/0149305 A1 | 7/2006 | Cuevas et al. | |
| 2006/0217666 A1 | 9/2006 | Wenchell | |
| 2006/0224120 A1 | 10/2006 | Smith et al. | |
| 2007/0197972 A1 | 8/2007 | Racenet et al. | |
| 2008/0011307 A1 | 1/2008 | Beckman et al. | |
| 2008/0097332 A1 | 4/2008 | Greenhalgh et al. | |
| 2009/0076464 A1 | 3/2009 | Gresham | |
| 2009/0076465 A1 | 3/2009 | Berry et al. | |
| 2009/0082720 A1 | 3/2009 | Smith | |
| 2009/0093682 A1 | 4/2009 | Izzo et al. | |
| 2009/0105635 A1 | 4/2009 | Bettuchi et al. | |

FOREIGN PATENT DOCUMENTS

| | | |
|---|---|---|
| EP | 0550069 A1 | 7/1993 |
| EP | 0 950 376 | 10/1999 |
| EP | 1629787 A2 | 3/2006 |
| EP | 1707133 A1 | 10/2006 |
| FR | 2710270 | 9/1993 |
| GB | 2 071 502 | 9/1981 |
| GB | 2 255 019 | 10/1992 |
| JP | 10-108867 | 4/1998 |
| JP | 2002-28163 | 12/2009 |
| WO | 94/04067 A1 | 3/1994 |
| WO | WO 95/04202 | 2/1995 |
| WO | WO 95/07056 | 3/1995 |
| WO | WO 95/22289 | 8/1995 |
| WO | WO 95/27445 | 10/1995 |
| WO | WO 95/27468 | 10/1995 |
| WO | 96/05881 | 2/1996 |
| WO | WO 98/35614 | 8/1998 |
| WO | WO 98/48724 | 11/1998 |
| WO | WO 99/25268 | 5/1999 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | 02/17800 A2 | 3/2002 |
| WO | 2006/110733 A2 | 10/2006 |
| WO | 2008/121294 A1 | 10/2008 |
| WO | 2008/149332 A1 | 12/2008 |

OTHER PUBLICATIONS

Corresponding Japanese Office Action, Application No. JP 2006-513313 dated Nov. 6, 2009.

European Search Report (3 pgs) for corresponding EP04750647, date of mailing Sep. 24, 2012.

European Search Report, Application No. EP 09 00 0060 dated Jun. 22, 2009. (7 pages).

European Search Report, Application No. EP 08253234, dated Jan. 30, 2009.

European Search Report, Application EP09250324, dated Jul. 15, 2011.

Extended European Search Report from European Patent Application No. 11250370.1 mailed Jun. 29, 2011.

* cited by examiner

SURGICAL HAND ACCESS APPARATUS

CROSS REFERENCE TO RELATED APPLICATIONS

This application is a divisional of U.S. application Ser. No. 10/832,224, filed Apr. 26, 2004, now U.S. Pat. No. 7,153,261 which, in turn, claims the benefit of and priority of U.S. Provisional Application Ser. No. 60/465,932, filed on Apr. 25, 2003, the entire contents of which are hereby incorporated by reference.

BACKGROUND

The present disclosure relates to surgical devices and more particularly to a surgical access device for use in a minimally invasive surgical procedure.

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. . . . However, despite its recent success and overall acceptance as a preferred surgical technique, minimally invasive surgery, such as laparoscopy, has several disadvantages. In particular, surgery of this type requires a great deal of surgeon skill in order for the surgeon to manipulate the long narrow endoscopic instruments about a remote site under endoscopic visualization. In addition, in laparoscopic surgery involving the intestinal tract it is often preferable to manipulate large sections of the intestines to perform the desired procedure. These manipulations are not practical with current laparoscopic tools and procedures accessing the abdominal cavity through a trocar or cannula.

SUMMARY

Accordingly the present disclosure is directed to an access device for use during a surgical procedure. The access device includes a housing defining a longitudinal axis and having a passageway therethrough dimensioned to permit passage of a surgeon's arm, and a fabric seal mounted within the opening. The fabric seal is dimensioned to form a substantial sealing relation with the surgeon's arm. The fabric seal is elongated extending along the longitudinal axis. The hand access device defines a constriction. For example, the fabric seal may define an hourglass configuration. The device may further include a pair of flexible bands which are mounted about the fabric seal to form a constriction. The flexible bands are adapted to engage an outer surface of the seal to bias the fabric seal to a constricted or closed position thereof. The flexible bands are connected to each other at respective end portions thereof and are arranged in opposed relation. The flexible bands are adapted to bow outwardly upon passage of the surgeon's arm through the fabric seal, and return to the constricted or closed position in the absence of the surgeon's arm. The fabric seal may include a lubricious coating.

In an alternate embodiment, an assembly for permitting access to a body cavity, includes a base retractor which is at least partially positionable within an opening in tissue and adapted to at least partially retract the tissue surrounding the opening. The base retractor defines a longitudinal axis and has a longitudinal channel extending along the longitudinal axis. The assembly further includes a hand access device mounted to the base retractor. The hand access device includes a housing member having a passageway dimensioned to permit passage of a surgeon's arm or hand and a fabric seal disposed within the housing member. The fabric seal defines a seal opening adapted to form a substantial sealing relation with the surgeon's arm or hand. The fabric seal is normally biased to a position wherein the seal opening is substantially closed.

At least one flexible band is mounted adjacent a periphery of the fabric seal. The flexible band is normally biased to engage the fabric seal and cause the fabric seal to assume a position where the seal opening is substantially closed. A pair of flexible bands may be mounted about the periphery of the fabric seal. The flexible bands are normally biased to engage the fabric seal to substantially close the seal opening thereof. The flexible bands are further adapted to move in a radial outward direction upon passage of the surgeon's arm or hand through the fabric seal. The flexible bands are connected at respective end portions thereof and are adapted to bow outwardly upon passage of the surgeon's arm or hand. The flexible bands may include slots therein to enhance flexibility.

The hand access device may be releasably mounted to the base retractor and preferably mounted for rotational movement relative to the base retractor.

BRIEF DESCRIPTION OF THE DRAWING(S)

Preferred embodiments of the present disclosure will be better appreciated by reference to the drawings wherein.

DETAILED DESCRIPTION OF THE PREFERRED EMBODIMENT(S)

The hand access apparatus of the present disclosure provides a substantial seal between a body cavity of a patient and the outside atmosphere before, during and after insertion of an object, e.g., a hand, through the apparatus. Moreover, the hand access apparatus of the present disclosure maintains a fluid tight interface about the arm to preserve the atmospheric integrity of a surgical procedure from gas and/or fluid leakage. Specifically, the hand access apparatus accommodates angular manipulation of the arm relative to a seal axis. This feature of the present disclosure desirably minimizes the entry and exit of gases and/or fluids to/from the body cavity.

The hand access apparatus may be used in conjunction with a base unit, e.g., a retractor base, which is positionable within an incision accessing, e.g., the abdominal cavity.

In the following description, as is traditional the term "proximal" refers to the portion of the instrument closest to the operator while the term "distal" refers to the portion of the instrument remote from the operator.

Referring now to the drawings, in which like reference numerals identify identical or substantially similar parts throughout the several views, FIGS. 1-4 illustrate an embodiment of a hand access apparatus of the present disclosure. Hand access apparatus 100 includes housing 102 defining a housing axis "a" extending the length of the axis "a" and seal 104 mounted within the housing 102. Housing 102 desirably incorporates several components assembled together to define a single unit, namely, main body 106 and end caps 108 connected at each end of the main body 106. The components of housing 102 may be fabricated from any conventional biocompatible rigid material including moldable polymeric materials, stainless steel or the like. End caps 108 are connected to the main body 106 through a compression fit and/or spot welding. Other means for securing these components are also envisioned. End caps 108 serve to secure seal 104 within housing 102 as will be discussed.

Seal 104 is preferably a fabric seal and is desirably arranged so as to have a constriction. For example, the seal may have the general shape of an hourglass. Each end 110 of seal 104 is secured to housing 102 by positioning the respective seal end 110 within a slot defined between each end cap 108 and main body 106 and thereafter securing the end cap 108 to the main body 106 via the aforedescribed compression fit. Other means for securing the seal ends 110 to housing 102 are also envisioned including adhesive means, spot welding, etc.

Seal 104 preferably includes a fabric material, such as woven material, a braided material, or a knitted material. The type of material is selected to provide a desired expansiveness. For example, a braid of varying end count and angle may be selected. Any natural or man-made material may be used for the fabric. In certain embodiments, a synthetic material such as nylon, Kevlar (Trademark of E.I. DuPont de Nemours and Company) or any other material that will expand and compress about an arm inserted through housing 102 is used. The selected material desirably minimizes or prevents the formation of gaps when the hand is introduced into housing 102. The material of seal 104 may be porous or impermeable to the insufflation gas. If porous, seal 104 may include a coating of an elastomeric material which is impermeable to the insufflation gas or at least a portion of the seal 104 may be coated. In addition, the fabric may be coated on its interior with urethane, silicon or other flexible lubricious materials to facilitate passage of the hand and arm through the fabric seal 104. In certain embodiments, the fabric is gathered about the axis "a" so as to form a constriction or closed portion. The fabric is desirably constructed of a material and/or arranged so that the fabric forms a constriction or closure. The seal may also be molded so as to have a constriction or may be knitted, braided or woven so as to have a constriction. For example, the seal 104 is desirably formed as disclosed in U.S. Provisional Patent Application Nos. 60/540,421, filed Jan. 30, 2004 and 60/466,005, filed Apr. 25, 2003, the disclosures of which are hereby incorporated by reference herein. For example, the fabric is desirably comprised of a plurality of strands woven, braided, or knitted together, and the strands may include multifilament and/or monofilament strands of polypropylene, nylon, polytetrafluoroethylene, such as Teflon (Trademark of E.I. DuPont de Nemours and Company), polyethylene terepthalate ("PET") and/or polyarylether-ether ketone ("PEEK"). The fabric is desirably molded, extruded, sprayed, dipped, corrugated or otherwise formed with an elastomeric material such as thermoplastic elastomers ("TPE"), polyurethane, polyisoprene, silicone, monprene, stanoprene.

With continued reference to FIGS. 1-4, in a preferred embodiment, seal 104 further includes a resilient member, such as a pair of flexible bands 112 which are positioned adjacent the midsection or neck of the seal 104. Flexible bands 112 are made of a suitable flexible material such as stainless steel, spring steel, shape memory metals, etc. . . . Flexible bands 112 are secured to the outer periphery of seal 104 with adhesives or the like or alternatively could be sewn onto or into the fabric. Flexible bands 112 are preferably pivotally connected at their respective ends with pivot pins 114. Flexible bands 112 are adapted to pivot about pivot pins 114 and bow outwardly from a closed position depicted in FIG. 4 to the open position depicted in FIG. 3 to permit passage of the hand and arm through housing 102. In alternative embodiments, the resilient member comprises a single member or more than two members operatively connected.

Figure 1:
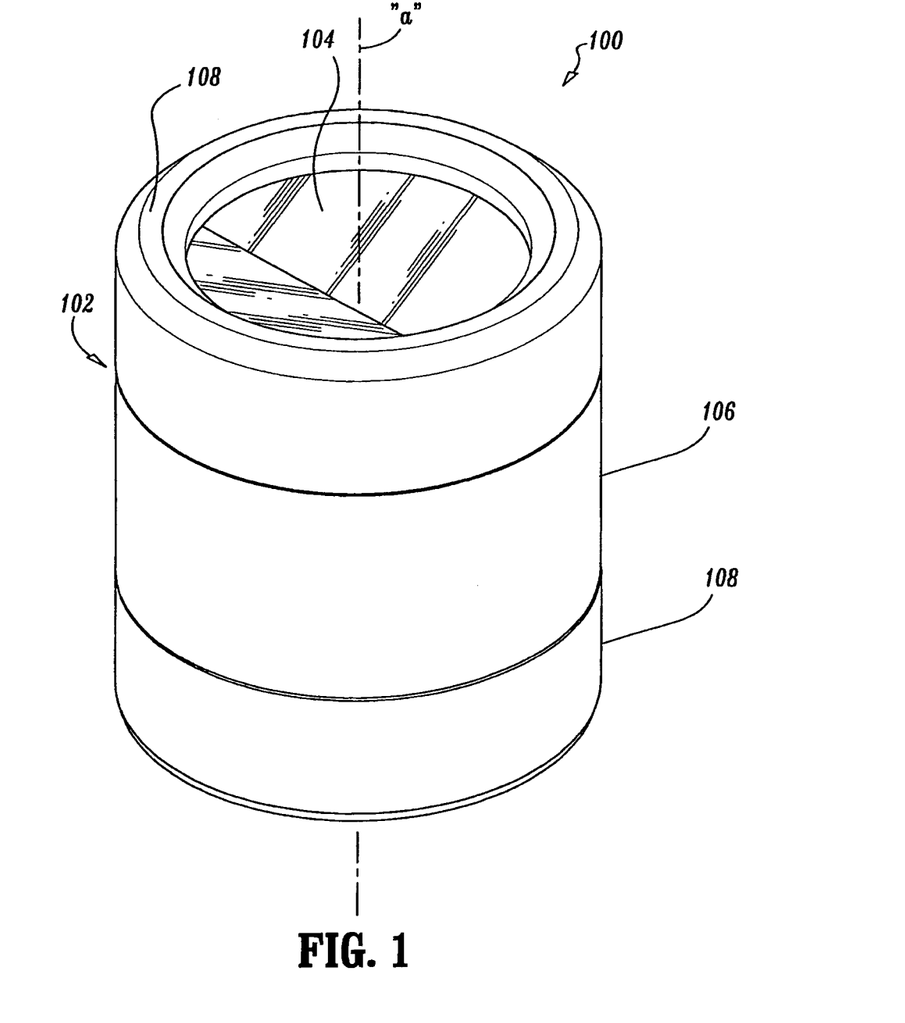
FIG. 1 is a perspective view of the hand access apparatus in accordance with an embodiment of the present disclosure.
Figure 2:
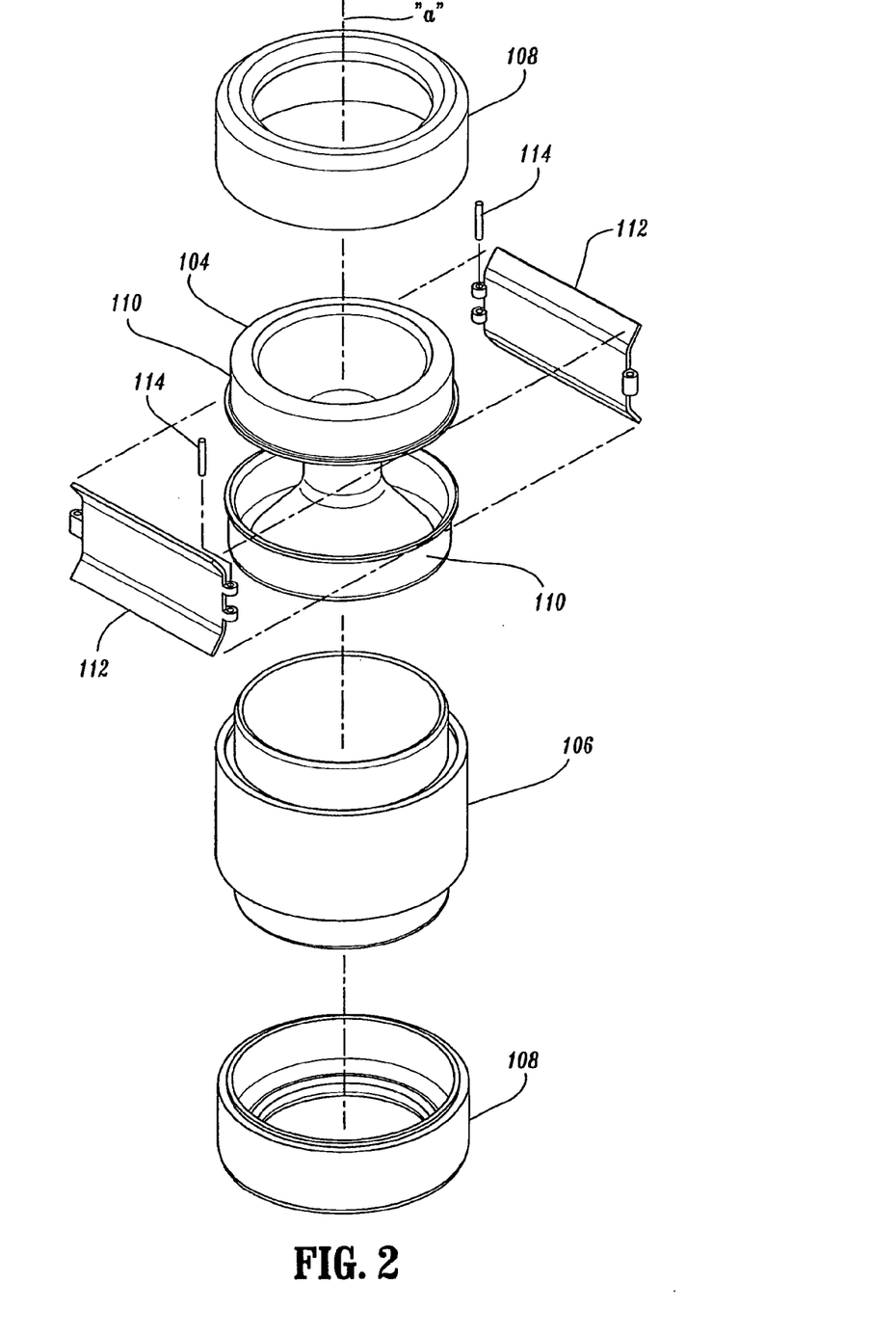
FIG. 2 is a perspective view with parts separated of the apparatus of FIG. 1.
Figure 3:
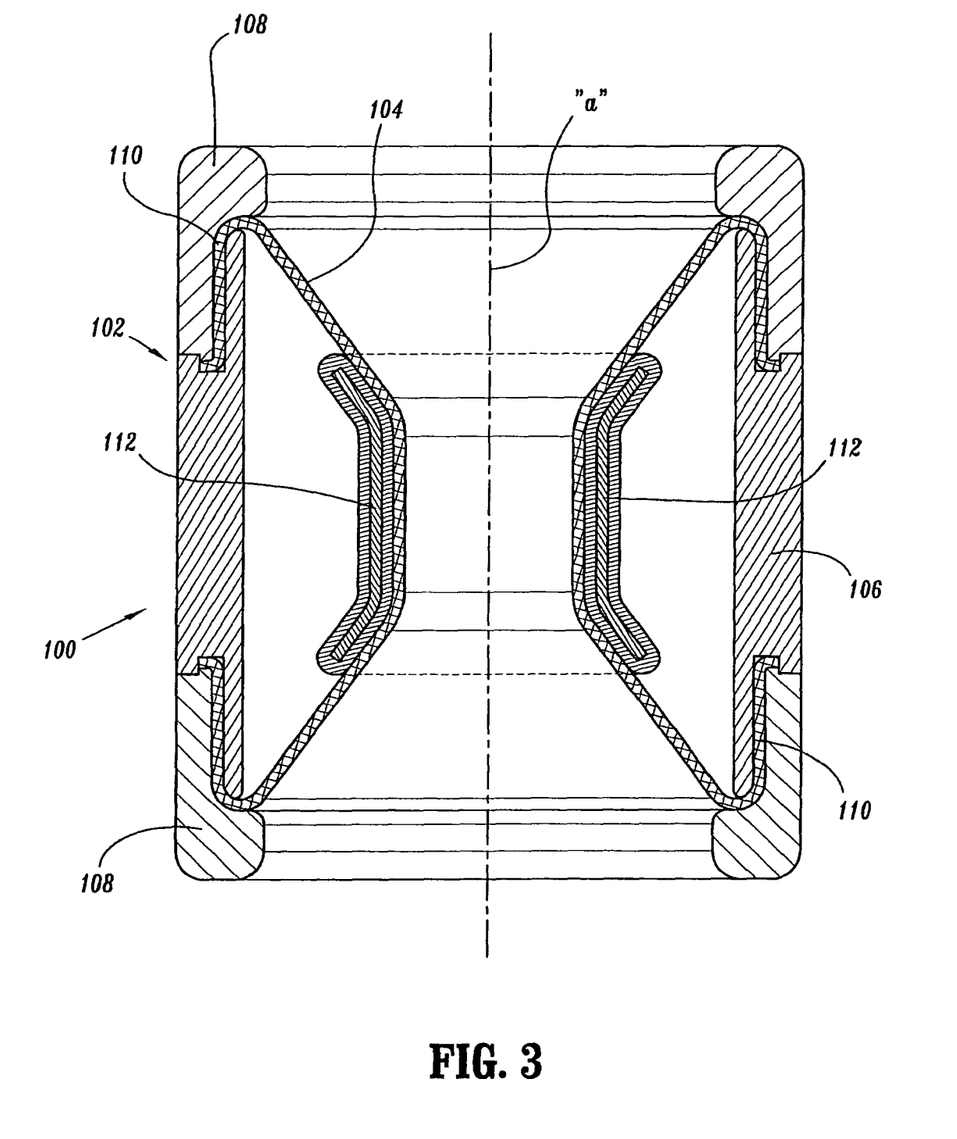
FIG. 3 is a cross-sectional view of the apparatus of FIG. 1.
Figure 4:
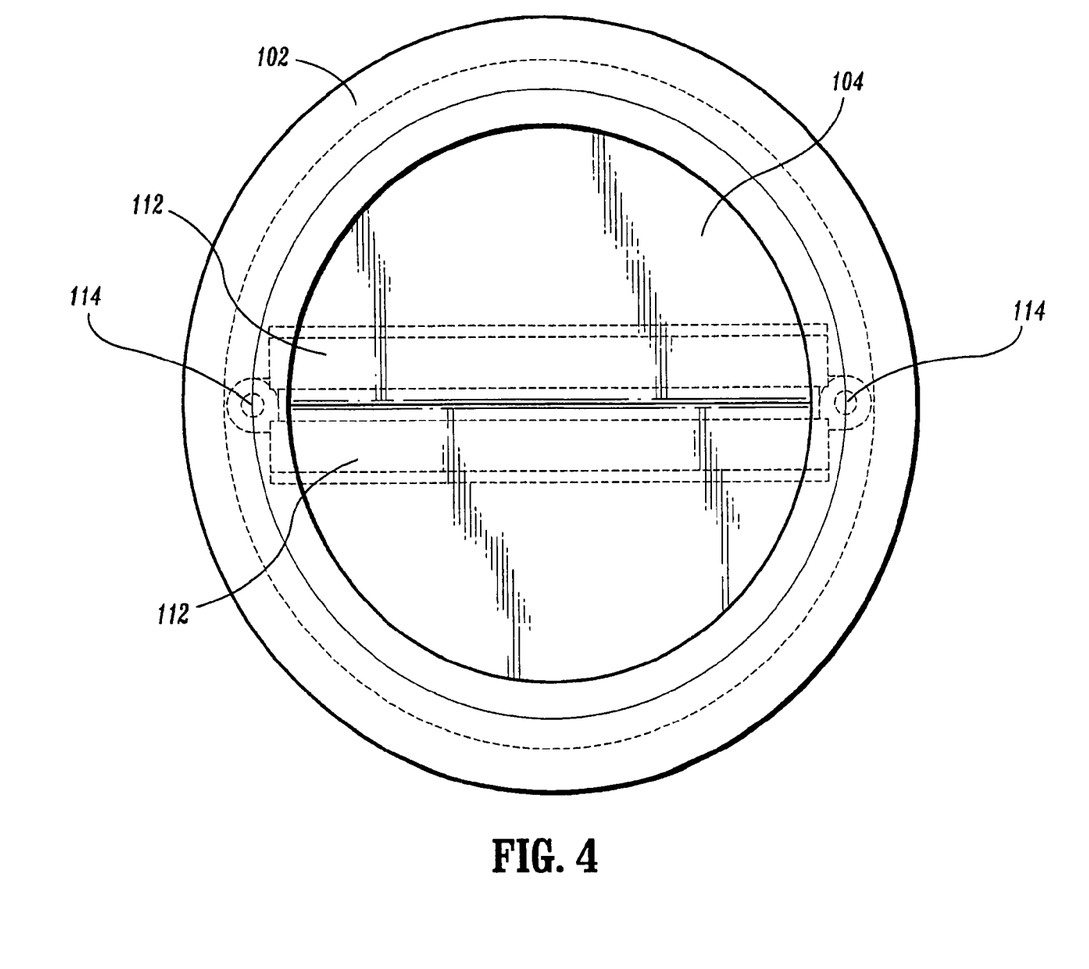
FIG. 4 is a top plan view of the apparatus of FIG. 1.

Flexible bands 112 are normally biased to the closed position and assume this position in the absence of the surgeon's hand to completely close the seal opening. Flexible bands 112 may be coated with either urethane, silicon or other flexible lubricious coating materials. Flexible bands 112 preferably possess an open u-shape in cross-section as depicted in FIGS. 1 and 3 to approximate the entry and exit funnel shape of the hour glass seal to thereby facilitate entry and exit movement of the surgeon's hand. In one embodiment, flexible bands 112 are moved to the open position of FIG. 3 by direct engagement with the surgeon's hand or arm passing through housing 102. It is also envisioned that a separate mechanism could be provided to manually open and close flexible bands 112 independent of the engagement with the hand of the surgeon. Other means of biasing the seal 104 closed may be used, such as foam supports, gel packing, pressurized fluid chambers, for example. In other embodiments, the biasing means is omitted. In further embodiments, the biasing means is omitted and an additional seal, such as a flapper valve or duck bill valve, is used in addition to seal 104.

Figure 5:
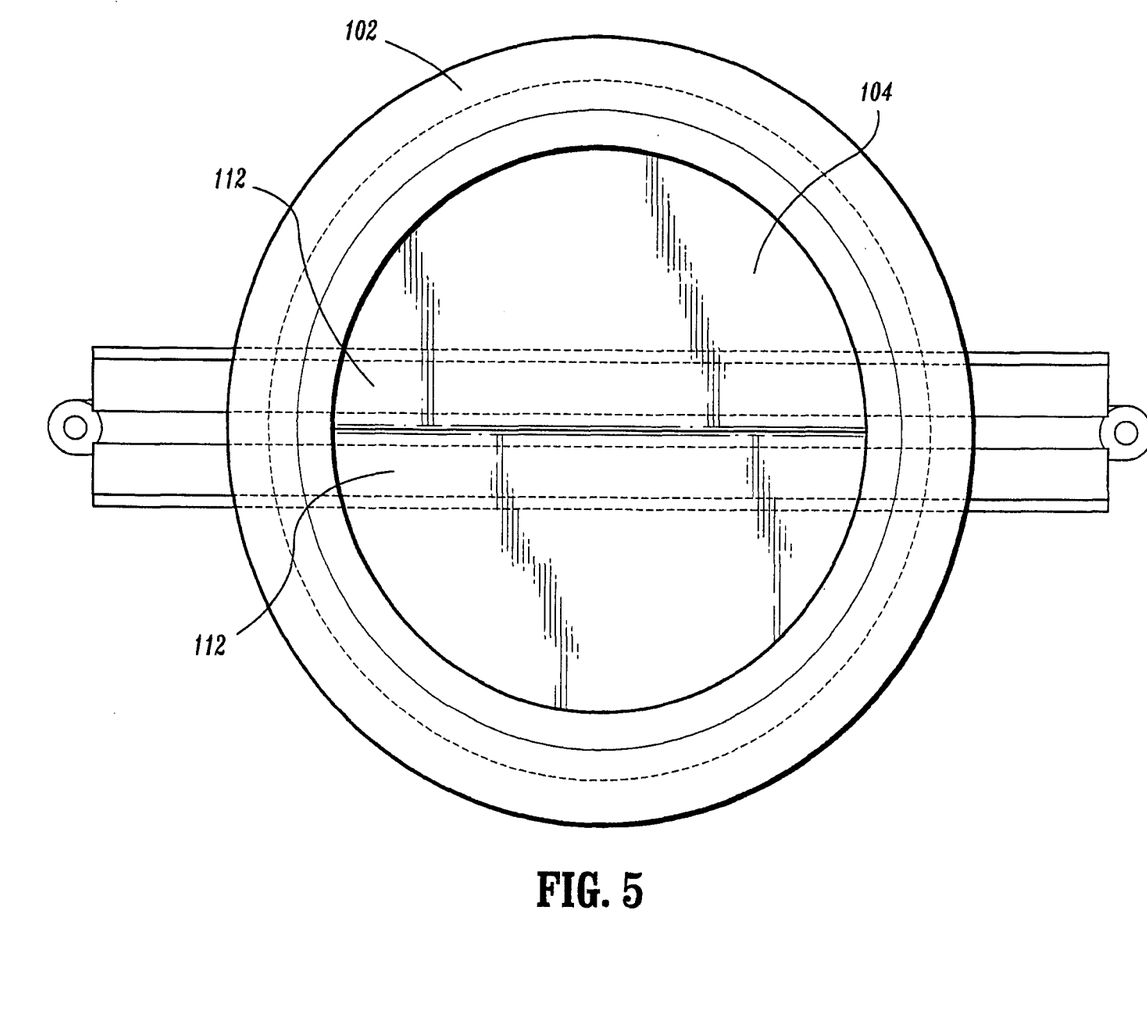
FIG. 5 is an alternate embodiment in accordance with the present disclosure.

FIG. 5 illustrates an alternate embodiment of the hand access apparatus of the present disclosure. This embodiment is substantially similar to the embodiment of FIGS. 1-4. However, with this embodiment, flexible bands 112 are greater in length to extend beyond the outer periphery of housing 102. With this arrangement, flexible bands 112 open to a larger dimensioned opening in the open configuration of the seal 104.

Figure 6:
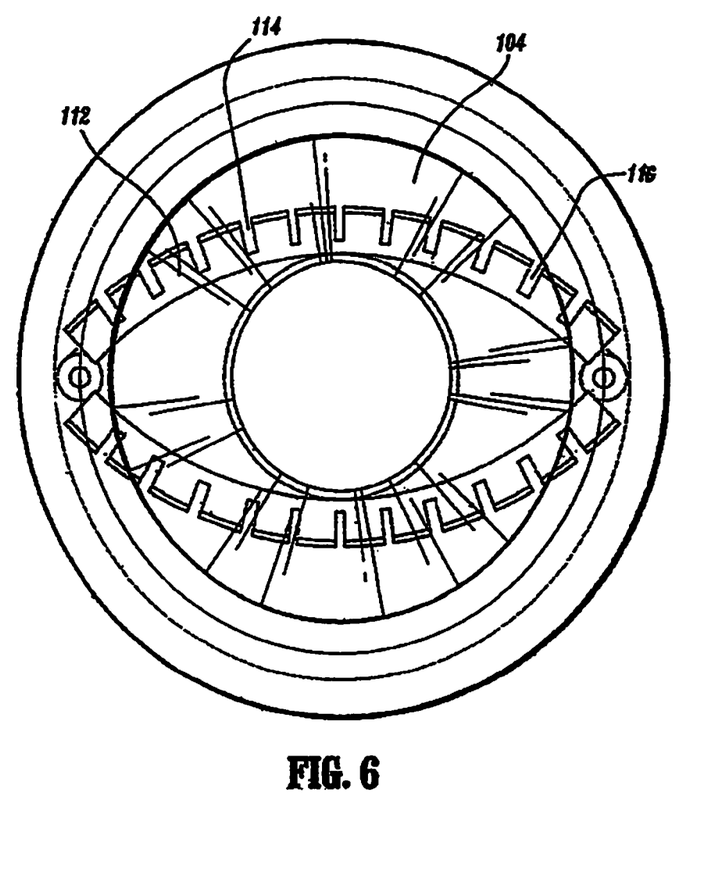
FIG. 6 is another alternate embodiment in accordance with the present disclosure.

FIG. 6 illustrates another alternate embodiment where the flexible bands 112 have a u-shaped cross-section and the legs of the u-shape include cuts or slots 116 to facilitate the bowing action.

Figure 7:
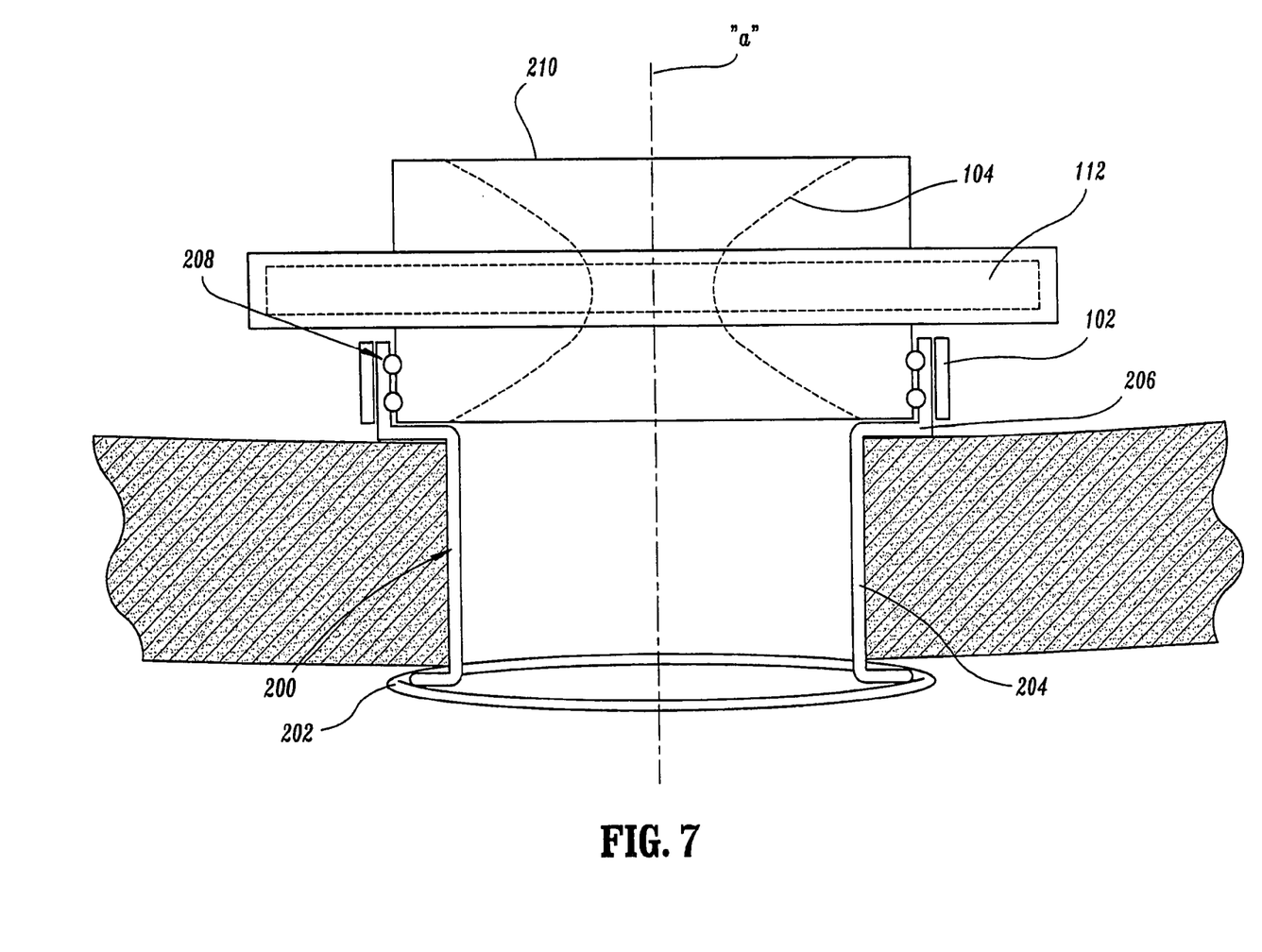
FIG. 7 is a view of a further embodiment in accordance with the present disclosure, including a retractor base.

With reference now to FIG. 7, there is illustrated a further embodiment having a hand access apparatus in combination with a base retractor unit 200 which is positioned within an opening in the abdominal wall. Base retractor unit 200 includes lower member 202, flexible sleeve 204 extending from the lower member 202 and upper member 206. Lower member 202 is positionable within the abdominal cavity. Preferably, lower member 202 is an elastomeric or resilient ring, such as a metallic, or polymeric ring which is suitably flexible to be deformed into an oblong shape to permit entry within the incision, but which returns to its normal annular shape upon release within the abdominal cavity. Suitable materials for lower member 202 include spring steel, shape memory metals, elastomeric materials, etc. . . . It is also envisioned that lower member 202 may be an annular inflatable member which is selectively inflatable to a desired configuration.

Flexible sleeve 204 is preferably fabricated from an impermeable medical grade material, e.g., including an elastomeric or latex material. The sleeve 204 is preferably tubular in shape and integral with or connected to lower member 202 through conventional means. Flexible sleeve 204 may be dimensioned to retract the tissue upon its deployment within opening and also serve as a barrier preventing fluids from entering the incision. Upper member 206 may be an elastomeric or resilient ring for tensioning the sleeve 204 and retracting the incision in the abdominal wall, such as a polymeric or metallic ring, or alternatively, an inflatable member similar in design to lower member 202.

Hand access apparatus 100 may be releasably mounted to base retractor unit 200 through conventional means including a snap or interference fit, or e.g., a bayonet coupling. Desirably, the upper member 206 includes a relatively rigid member to facilitate the mounting of the apparatus. In one preferred arrangement, base retractor unit 200 includes a quick connect detent or ball bearing mechanism, identified generally as reference numeral 208, to connect the two components. With this arrangement, the ball bearings are arranged to engage corresponding annular recesses in the exterior of housing 102. In this regard, hand access apparatus 100 may swivel or rotate about axis "a" relative to the base retractor unit. Other means for connecting the two components are envisioned as well, such as latches, bayonet connections, etc. An o-ring seal may be provided to prevent loss of fluid through the components. It is also envisioned that a second zero-closure valve 210 may be mounted to the proximal end of hand access apparatus 100 or to base retractor unit 200. This valve 210 may be a duckbill, flapper, single slit or double slit zero-closure valve, an iris valve or seal comprised of gel materials. The second valve 210 may remove the need for the fabric seal 104 to completely close in its unexpanded state. In further embodiments, the upper member 206 of the base retractor unit comprises at least one tab for engaging and fixing the sleeve 204 after tensioning.

In use in a laparoscopic procedure, an incision is made in the abdominal wall of the insufflated abdominal cavity. Base retractor unit 200 is positioned within the incision by deforming lower member 202 to a narrow configuration to pass through the opening and thereafter releasing the member within the abdominal cavity. Flexible sleeve 204 thus lines the incision with the outer member disposed exterior of the body. Preferably, the sleeve is tensioned so as to retract the incision. Thereafter hand access apparatus 100 is mounted to base retractor unit 200 in the aforedescribed manner. The surgeon thereafter passes his hand and arm through seal 104 whereby the flexible bands 112 bow outwardly. Seal 104 engages the arm in substantially fluid tight manner to prevent release of insufflation gases. Surgery is then performed with the seal permitting off-axis manipulation of the arm while maintaining the desired seal about the arm. Upon completion, the surgeon's arm is withdrawn and the seal 104 returns to its normal constricted position closing seal 104 and preventing gasses from escaping through the apparatus.

While the invention has been particularly shown, and described with reference to the preferred embodiments, it will be understood by those skilled in the art that various modifications and changes in form and detail may be made therein without departing from the scope and spirit of the invention. For example, the resilient member disposed around the fabric seal may comprise an elastomeric band, or other resilient member. Accordingly, modifications such as those suggested above, but not limited thereto, are to be considered within the scope of the invention.

What is claimed is:

1. An assembly, which comprises:
   a base retractor at least partially positionable within an opening in tissue and adapted to at least partially retract the tissue surrounding the opening, the base retractor defining a longitudinal axis and having a longitudinal channel extending along the longitudinal axis;
   a hand access device mounted to the base retractor, the hand access device including a housing member having a passageway dimensioned to permit passage of a surgeon's arm or hand and a fabric seal disposed within the housing member, the fabric seal defining a seal opening adapted to form a substantial sealing relation with the surgeon's arm or hand; and
   a pair of flexible bands mounted about the periphery of the fabric seal, the flexible bands normally biased to engage the fabric seal to substantially close the seal opening thereof, the flexible bands further adapted to move in a radial outward direction upon passage of the surgeon's arm or hand through the fabric seal.

2. The assembly according to claim 1 wherein the flexible bands are connected at respective end portions thereof and are adapted to bow outwardly upon passage of the surgeon's arm or hand.

3. The assembly according to claim 2 wherein the flexible bands include slots therein.

4. The assembly according to claim 1, wherein the fabric seal generally defines an hourglass configuration.

5. The assembly according to claim 1, wherein the flexible bands are connected to each other at respective end portions about respective pivot pins.

6. The assembly according to claim 1, wherein the fabric seal comprises a lubricious coating.

7. The assembly according to claim 1, wherein the fabric seal includes an elastomeric material formed with fabric material of the fabric seal.

8. The assembly according to claim 1, wherein the fabric seal is coated with an elastomeric material.

9. The assembly according to claim 1, wherein the housing member is mounted for rotational movement relative to the base retractor.

* * * * *